United States Patent
Kwasniewski et al.

[11] Patent Number: 5,863,420
[45] Date of Patent: Jan. 26, 1999

[54] UNSATURATED HYDROCARBON SEPARATION AND RECOVERY PROCESS

[76] Inventors: Vincent J. Kwasniewski, 1949 Sunnyside Cir., Northbrook, Ill. 60062; Narasimhan Calamur, 61 Portwine Rd., Willowbrook, Ill. 60514; Mark P. Kaminsky, 0S 344 Summit Dr., Winfield, Ill. 60190; John A. Mahoney, 816 Lenox Rd., Glen Ellyn, Ill. 60137; Charles G. Scouten, 29W528 Forestview Dr., Warrenville, Ill. 60555-2101; Richard A. Wilsak, 432S Sleight St., Naperville, Ill. 60540

[21] Appl. No.: 730,093

[22] Filed: Oct. 15, 1996

[51] Int. Cl.[6] ............ C10G 25/00; B01D 53/22; C07C 7/144; C07C 7/10
[52] U.S. Cl. .................. 208/308; 95/45; 95/50; 585/818; 585/819; 585/844; 585/840; 585/834
[58] Field of Search ............... 585/818, 840, 585/814, 844, 835, 834, 839, 833; 208/308; 95/45, 50; 90/9, 10

[56] References Cited

U.S. PATENT DOCUMENTS

| | | | |
|---|---|---|---|
| 3,758,605 | 9/1973 | Hughes et al. | 260/677 A |
| 3,800,506 | 4/1974 | Hughes et al. | 55/16 |
| 4,750,918 | 6/1988 | Sirkar | 55/16 |
| 5,057,641 | 10/1991 | Valus et al. | 585/818 |
| 5,135,547 | 8/1992 | Tsou et al. | 55/16 |

FOREIGN PATENT DOCUMENTS

0634204A1  1/1995  European Pat. Off. .

OTHER PUBLICATIONS

Majumdar et al., "A New Liquid Membrane Technique for Gas Separation," A.I. Ch. E. Journal, vol. 34, No. 7, pp. 1135–1145 (Jul. 1988).

Primary Examiner—Hien Tran
Assistant Examiner—Thuan D. Dang
Attorney, Agent, or Firm—James R. Henes; Stephen L. Hensley

[57] ABSTRACT

A process disclosed for the separation, purification and recovery of an unsaturated hydrocarbon from its mixture with at least one other material using a facilitated transport liquid membrane system.

17 Claims, 1 Drawing Sheet

UNSATURATED HYDROCARBON SEPARATION AND RECOVERY PROCESS

BACKGROUND OF THE INVENTION

1. Field of the Invention

The present invention relates to a process for the separation and recovery of an unsaturated hydrocarbon using a facilitated transport liquid membrane system, and more particularly concerns the aforesaid process with purification of the unsaturated hydrocarbon.

2. Discussion of the Prior Art

There currently exist a number of methods for the selective separation of gaseous feed stream components, including the removal of an unsaturated hydrocarbon from a gas stream containing a mixture of the unsaturated hydrocarbon with a saturated hydrocarbon.

Facilitated transport membrane technology is a known separation technique. It has been demonstrated in the laboratory for the selective separation of a gas stream component, such as the removal of an unsaturated hydrocarbon from a feed stream containing a mixture of the unsaturated hydrocarbon and at least one other material. The agent used normally to facilitate the transport is a complexation agent that contains a metal ion that has an affinity for the unsaturated hydrocarbon to be separated. The silver ion is known to be especially useful for the separation of olefins.

Sirkar, U.S. Pat. No. 4,750,918 discloses a type of facilitated transport involving the use of hollow fiber membranes, as opposed to flat sheet membranes. In this patent, the feed and recovery hollow fibers are immersed in a liquid bath to avoid drying problems often encountered with flat sheet immobilized membranes. The gases permeate through the wall of the feed hollow fiber, diffuse across the liquid bath and permeate into the bore of the recovery hollow fiber.

S. Majumdar et al., "A New Liquid Membrane Technique for Gas Separation," *A. I. Ch. E. Journal*, Vol. 34., No. 7, pages 1135–1145, discloses a liquid membrane separation technique for gas mixtures in which feed and sweep gases flow through the lumen of two different sets of hydrophobic microporous hollow fibers while a liquid on the shell side acts as the membrane. The technique involves the use of a dense population of hydrophobic microporous hollow fibers of small outside diameter and a permeator shell. In such a hollow-fiber assembly, the space between the adjacent fibers is filled with an aqueous liquid chosen to function as a liquid membrane. One set of hollow fibers carries the high-pressure feed gas while a second set of hollow fibers carries a sweep gas, usually at a pressure considerably lower than the feed pressure. Ideally, the fiber bundle is arranged in such a way that a feed gas-carrying fiber is immediately adjacent to a sweep gas-carrying fiber. Water and aqueous electrolytic solutions do not penetrate the pores of these hydrophobic fibers unless the liquid pressure exceeds 10–15 atmospheres. The feed gas, species contact the membrane liquid at the pore mouths at the outside surface of the feed fiber. They dissolve at this feed gas membrane liquid interface and diffuse through the liquid membrane to the open pores at the outside surface of the nearest sweep fiber, where they desorb. The desorbed gases are carried away through the sweep fiber lumina by an inert sweep gas. The membrane liquid between the fibers is usually stationary. Z. Qi et. al., "Microporous Hollow Fibers for Gas Absorption," *J. Membrane Sci.*, Vol. 23, page 321 (1985), also discloses the use of two hydrophobic microporous hollow-fiber modules for gas separation, one in the sorption mode and the other in the desorption mode.

R. Creusen et al., European Patent Application No. 94201995.1, filed on Jul. 11, 1994 and published on Jan. 18, 1995 as Publication No. 0634204 A1, discloses a process and device for the separation of an unsaturated hydrocarbon from a fluid mixture containing saturated hydrocarbons in which in a first stage the fluid mixture is passed at superatmospheric pressure to one side of a first semiselective gas separation membrane with a non-porous active layer, and a liquid complexing agent is passed along the other side of such first membrane, where the unsaturated hydrocarbon is bound through complexation at the interface of the membrane and the complexing agent. In a second stage, the unsaturated hydrocarbon is dissociated from the complexing agent through a temperature increase, and the resulting mixture of the complexing agent and dissociated unsaturated hydrocarbon is separated, and the complexing agent is then recycled. Preferably the mixture of complexing agent and dissociated, unsaturated hydrocarbon is passed at superatmospheric pressure to one side of a second semiselective membrane with a non-porous active layer wherein the unsaturated hydrocarbon migrates to the other side of the second membrane and is discharged. The disclosed advantage of such process and device is that the process of sorption involving the complexation reaction in the first stage is separate and independently adjustable from the process of desorption involving the dissociation reaction in the second stage and that a substantial dissociation of the complex formed can be obtained by using a temperature increase.

However, while there has been interest in using membranes as a means of separation, the lack of highly selective membranes has hindered the application of membranes for this purpose. The problem associated with all facilitated transport processes is that materials which do not form complexes with the complexation agent but which are at least somewhat soluble in the liquid solution of the complexing agent, as well as the unsaturated hydrocarbons that actually form complexes with such agent, are removed from the fluid feed mixture in the sorption process and recovered with the unsaturated hydrocarbons in the dissociation process. Therefore, facilitated transport processes in general are less selective for the separation and recovery of the unsaturated hydrocarbons than the chemistry alone would suggest. In addition, more than one unsaturated hydrocarbon may form complexes with the complexing agent. Consequently, it is highly desirable to improve the selectivity for the recovery of each separated unsaturated hydrocarbon in facilitated transport processes without an unacceptably large reduction in the yield of unsaturated hydrocarbons recovered.

OBJECTS OF THE INVENTION

It is therefore a general object of the present invention to provide an improved aforesaid process of separation and recovery that affords the aforesaid desirable features and overcomes the aforesaid problems.

More particularly, it is an object of the present invention to provide an improved aforesaid process that maximizes the selectivity for the recovery of each separated unsaturated hydrocarbon.

It is a related object of the present invention to provide an improved aforesaid process that maximizes the selectivity for the recovery of each separated unsaturated hydrocarbon without an unacceptably large reduction in the yield of each recovered unsaturated hydrocarbon.

It is another object of the present invention to provide an improved aforesaid method that permits independent control and optimization of each of the process of separating and of recovering each unsaturated hydrocarbon.

Other objects and advantages of the present invention will become apparent upon reading the following detailed description and appended claims.

SUMMARY OF THE INVENTION

These objects are achieved by the process of the present invention for the separation, purification and recovery of an unsaturated hydrocarbon from a mixture thereof with at least one other component in a multi-component feed gas. The process of this invention comprises: (a) contacting, through the micropores of a first hydrophobic microporous hollow fiber membrane, the feed gas flowing on one side of the membrane and an aqueous liquid solution of a complexing agent on the other side of the membrane, under conditions (i) such that the aforesaid complexation agent has a substantially greater affinity to form a reversible water-soluble complex with the aforesaid unsaturated hydrocarbon such that a substantial portion of the unsaturated hydrocarbon dissolves in the aqueous solution, and (ii) such that a portion of at least one uncomplexed component of the feed gas dissolves in the aqueous solution; (b) separating the resulting aqueous solution from the membrane employed in step (a); (c) subjecting the aqueous solution separated in step (b) to purification conditions such that the aforesaid uncomplexed component dissolved therein is substantially removed therefrom and the aforesaid complex of the unsaturated hydrocarbon remains substantially stable and dissolved in the aqueous solution; (d) contacting, through the micropores of a second hydrophobic microporous membrane, the aqueous solution resulting from step (c) and flowing on one side of the second membrane, with a gas phase on the other side of the second membrane and containing a substantially lower concentration of the aforesaid unsaturated hydrocarbon than its equilibrium concentration in the aqueous solution from step (c), under conditions such that the aforesaid complex dissociates in the aqueous solution and the resulting dissociated unsaturated hydrocarbon is substantially stripped into the gas phase on the other side of the second membrane; and (e) separating the resulting phase gas from the membrane employed in step (d).

BRIEF DESCRIPTION OF THE FIGURES

For a more complete understanding of this invention, reference should now be made to the embodiments illustrated in greater detail in the accompanying figures and described below by way of examples of the invention. In the figures.

Figure 1:
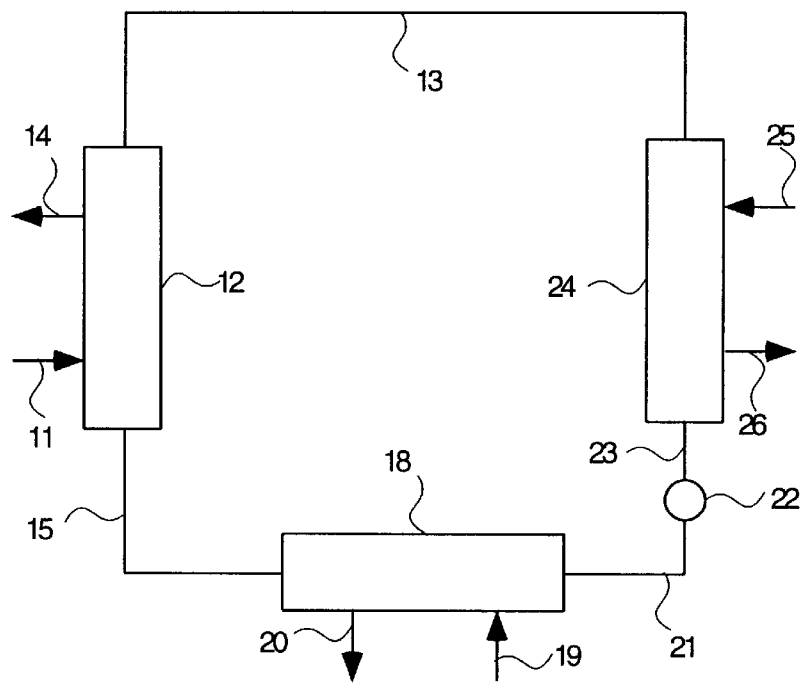
FIG. 1 is a schematic illustration of one preferred embodiment of the process of the present invention in which one unsaturated hydrocarbon is separated from a saturated hydrocarbon in a multi-component feed gas and is purified and recovered.

It should be understood, of course, that the invention is not necessarily limited to the particular embodiments illustrated herein.

DETAILED DESCRIPTION OF THE PREFERRED EMBODIMENTS

The method of the present invention is useful for separating at least one unsaturated hydrocarbon, such as an alkene, alkyne or aromatic compound, from a mixture thereof with at least one other material, such as an alkane, or another unsaturated hydrocarbon, or an inorganic gas like hydrogen or nitrogen, in a wide variety of multi-component gas streams. Suitable streams include many streams that are typically present in petroleum refineries and chemical plants. The streams in a petroleum refinery or chemical plant that are especially suitable as the multi-component feed gas in the method of the present invention are waste streams or recycle streams. Such streams often contain mixtures of either ethylene and ethane or propylene and propane, or both such mixtures, as well as other components. For example, offgas from a catalytic cracking unit in a refinery generally contains a mixture of ethylene, ethane, methane and hydrogen. In addition, the feed to an alkylation unit typically contains propylene admixed with contaminant propane; and separation of the propylene from propane would permit a higher propylene content feed stream and an effective debottlenecking of the alkylation unit. In chemical plants, ethylene is invariably present in a recycle stream employed as a portion of the feed to an olefins production unit and in an overhead stream from a demethanizer employed in the treatment of the resulting olefins products. Ethylene or propylene or both are also components in various vent streams or as contaminants in various feedstocks in chemical plants. All such streams are suitable sources of mixtures from which one or more unsaturated hydrocarbons can be separated by the method of the present invention. In general, the numerous processes that produce streams containing unsaturated hydrocarbon products are sources of suitable feed streams for use in the method of the present invention.

The reactivity of unsaturated hydrocarbons, in particular, unsaturated aliphatic hydrocarbons, with complexing metal ions generally decreases from acetylenes to dienes to monoolefins; and many other materials such as saturated hydrocarbons, in particular, saturated aliphatic hydrocarbons, and inorganic gases like nitrogen or hydrogen, are essentially unreactive towards the complexing metal ions. In addition, the various members of a given one of these aforesaid types of unsaturated aliphatic hydrocarbons often exhibit different reactivities towards a given complexing metal ion. Thus, on the basis of such differences, the process of the present invention can be used to separate parrafins from monoolefins, diolefins from monoolefins, diolefins from acetylenes, or acetylenes from paraffins, monoolefins and diolefins; as well as to separate a given unsaturated aliphatic hydrocarbon in one of the aforesaid classes from another member of the same class where different members of the same class react with the complexing metal ions to form complexes of different stability or at different rates.

Hydrophobic microporous hollow fiber membranes that are suitable for use in the process of the present invention are well-known and are readily available commercially. The compositions of the hydrophobic microporous hollow fiber membranes employed in the process of the present invention are not critical. The hydrophobic microporous hollow fiber membranes employed should be inert to the potentially harsh solvating power of the aqueous solution of the complexation agent, which often may have a high salt concentration. Suitable membranes for use in the process of the present invention should also be strong enough to withstand the operating pressures employed in the process of the present invention without bursting or collapsing. Polysulfone, polypropylene, or polyethylene hollow fibers or hollow fibers of copolymers of ethylene and propylene are preferred because they have high porosity and strength.

Since the membranes employed in the process of the present invention are hydrophobic, an aqueous solvent has a tendency not to enter the pores of the hydrophobic membrane, by contrast to the greater tendency of an aqueous solvent to enter into the pores of a hydrophilic membrane. Because the aqueous solution containing the complexation agent does not wet the hydrophobic membranes employed, the resistance to the permeation of gas components through the hydrophobic microporous hollow fiber membranes employed in the process of the present invention is very low. Thus, the pores of the hydrophobic membranes are available as a path for gas-phase diffusion, and the resulting gas permeation rate is much faster than that through pores filled with an aqueous solution in a hydrophilic membrane. Thus, since a hydrophobic membrane is employed, either the membrane can have a relatively larger average pore size or a lower pressure is needed to prevent the aqueous solvent from entering into such pores or both, than when a hydrophilic membrane is employed.

The complexation agent to be employed in the process of the present invention is selected such that the complexation agent is stable and soluble in water and the complex selectively formed from it and the unsaturated hydrocarbon component(s) of the feed gas is also stable and soluble in water and will readily form under the conditions employed in step (a) of the process of the present invention and yet will also readily dissociate under the appropriate shift in temperature, pressure, etc. in step (d) of the process of the present invention. In addition, the complexation agent employed in the process of the present invention should not react with any components of the unsaturated hydrocarbon-containing feed gas to form an insoluble material which could block the membrane pores or otherwise prevent separation or recovery of the desired unsaturated hydrocarbon component(s) of the feed gas. However, it is often possible to minimize or totally eliminate any problems resulting from the formation of a small amount of insoluble material by the removal of a slip stream of the aqueous solution and the replacement of it with a slip stream of fresh aqueous solution of the complexation agent.

Complexation agents which are sufficiently soluble and stable in water and which form reversible water soluble complexes with the unsaturated hydrocarbon or hydrocarbons to be separated in the process of the present invention include water soluble salts or complexes of the transition metals of the Periodic Chart of Elements having atomic numbers above 20. Such metals include those of the first transition series having atomic numbers from 21 to 29, such as chromium, copper, especially the cuprous ion, manganese, and the iron group metals; for example, nickel and iron. Other useful complex-forming metals are in the second and third transition series and have atomic numbers from 39 to 47 or 57 to 79, as well as mercury, particularly as the mercuric ion. Thus, noble metals such as silver, gold and the platinum group, among which are platinum, palladium, rhodium, ruthenium and osmium, can be employed in the method of the present invention. The useful metals of the second and third transition series include, for example, molybdenum, tungsten, and rhenium. Various combinations of these complexing-forming metals may also be employed in the method of the present invention, either in the presence or absence of other non-complexing metal cations or non-metal ions. The complex-forming metal is employed in the process of the present invention in the form which is soluble in water. Thus, the various water-soluble salts of the aforesaid metals, such as the nitrates and halides, for instance, the bromides and chlorides, fluoroborates, flurosilicates, acetates, carbonyl halides and other salts of these metals, can serve to form the desired water-soluble complexes. In general, silver, salts and complexes have been disclosed as preferred complexation agents in this application.

In addition, Dubois et al., U.S. Pat. Nos. 5,391,791; 5,414,194; and 5,430,225 disclose novel molybdenum sulfide dimer compounds and their use in olefin separation and acetylene removal processes. The disclosed dimers are disclosed as complexation agents for the olefins and acetylenes wherein the sulfide ligands of the molybdenum-sulfide dimers act as the site of olefin binding. The dimers disclosed have the general formula

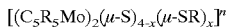

where x is 0–3 and n is 0, +1, or −1. In addition, this structure can be modified in a limited number of ways, such as substitutions that can be made to the alkanedithiolate moiety R or to the cyclopentadienyl moiety $C_5H_5$, in order to enhance the water solubility of the dimer or to introduce chemically reactive ligands that can be used to incorporate the dimer within the matrix of polymeric materials, such as membranes. The patents define suitable water soluble molybdenum-sulfide dimers as including all compounds that contain molybdenum and sulfur and that are capable of forming chemically or thermally-reversible alkanedithiolate or alkenedithiolate complexes that have significant solubility in water or aqueous systems.

The dimeric complexation agents are disclosed as being useful in separation processes that include liquid/liquid, gas/liquid, liquid/solid and gas/solid separation procedures that are familiar to those skilled in the art. Separations by the use of the molybdenum-sulfide dimers that are disclosed include the separation of olefins from paraffins (for example, ethylene from ethane and propylene from propane), the separation of olefins (for example, ethylene from propylene), the separation of olefin isomers (for example, cis-2-butene from trans-2-butene), the separation of olefins from alkynes (for example, ethylene from acetylene and propylene from propyne), and the removal of alkynes from a gaseous hydrocarbon feed stream and the catalytic reduction of alkynes.

The molybdenum sulfide dimers disclosed in the aforesaid Dubois et al. patents were synthesized in accordance with the procedures of Dubois et al., *J. Am. Chem. Soc.*, vol. 101, pages 5245–5252 (1979); Dubois et al., *J. Am. Chem. Soc.* vol. 102, page 7456 (1980). Dubois et al., *Inorg. Chem.*, vol. 20, pages 3064–3071 (1981); M. McKenna et al., *J. Am. Chem. Soc.*, vol. 105, pages 5329–5337 (1983); and J. Birnbaum et al., *Organometallics*, vol. 10, pages 1779–1786 (1991). However, generally such syntheses are lengthy and complicated and afford a low yield of the desired product. Also such product often must be modified further in order to achieve the necessary water solubility. Consequently, it is highly desirable to develop alternative materials that could be used as suitable complexation agents for the selective and reversible complexation of unsaturated hydrocarbons in the aforesaid processes for separating unsaturated hydrocarbons from hydrocarbon mixtures containing them.

Furthermore, R. Wilson, K. E. Meyer and M. F. Asaro, U.S. patent application Ser. No. 08/732,514, filed concurrently herewith, discloses the single cubane-type cluster of the formula

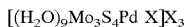

wherein X is a halide, as a suitable complexation agent for use in complexing and separating unsaturated hydrocarbons from their mixtures with at least one other component. This complexation agent is prepared in accordance with the following two-step procedure when X is chloride:

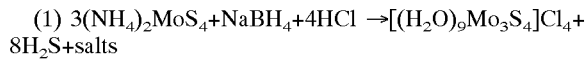

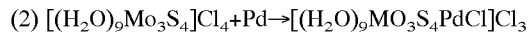

The concentration of the complexation agent employed in the process of the present invention must be sufficient to provide an adequate complexing weight. However, the aqueous solution must be less than saturated with respect of the complex-forming metal ions in order to ensure that all of the metal stays in solution, thereby avoiding any tendency to plug the pores of the membrane and destroy its permeability characteristics, without the need for the aforesaid use of a slip stream of fresh aqueous solution of the complexation agent.

A distinct advantage of the process of the present invention is that each aforesaid complexation step (step (a)), purification step (step (c)) and dissociation step (step (d)) is a distinct operation and is performed in a distinct unit or module and can therefore be controlled independently of one another. Thus, the process of the present invention affords greater flexibility in performing each of the aforesaid steps and in optimizing the conditions employed in each of the aforesaid steps, without any deleterious effect on the function of any other of such steps. In general, the specific complexation agent, complexation conditions, purification conditions and dissociation conditions employed in the method of the present invention depend on the composition of the multicomponent feed gas, the component or components of the feed gas to be separated and recovered, the other component or components of the feed gas which do not form complexes with the complexation agent employed, but which are soluble to some extent in the complexation solution, the desired purity and yield of each of the components to be separated and recovered, and the relative stability and relative ease of formation of and of dissociation of the complex of each component to be separated and recovered.

For example, the complexation conditions employed in step (a) of the process of the present invention include the specific complexation agent used, its concentration in and the pH of the aqueous solution, relative amounts of aqueous solution and feed gas, length of contact time, and a first temperature and a first pressure, such that the unsaturated hydrocarbon in the feed gas to be separated forms a reversible complex with the complexation agent and is substantially absorbed from the feed gas and complexed in the aqueous phase containing the aforesaid complexation agent while at least one other component of the feed stream, which component does not form a complex with the complexation agent, dissolves to some extent in the aqueous solution. For illustrative purposes only, such dissolved, uncomplexed other component is frequently referred to herein as a saturated hydrocarbon but can also be another unsaturated hydrocarbon or inorganic gas such as nitrogen or hydrogen. Also for illustrative purposes only, in step (a) as well as in steps (c), (d) and (g) as described hereinbelow, the liquid phase is frequently described as being on the exterior surface of the hollow fiber membrane and the gas phase or stream of stripping gas is frequently described as being on the inside of the hollow fiber membrane. However, it must be noted that the liquid phase could also be on the inside, and the gas phase could also be on the outside of the hollow fiber membrane. It is necessary only that the liquid and gas phases are on opposite sides of the membrane.

When the unsaturated hydrocarbon is ethylene or propylene, the first temperature employed in step (a) is suitably in the range of from about −10° C., preferably from about 0° C., more preferably from about 5° C., to about 300° C., preferably to about 250° C., more preferably to about 70° C. The first pressure employed in step (a) is suitably in the range of from about 0, preferably from about 25, more preferably from about 50 pounds per square inch gauge, to about 1000, preferably to about 600, more preferably to about 300 pounds per square inch gauge.

Then after separating in step (b) the aqueous solution containing the dissolved complex of each aforesaid unsaturated hydrocarbon and aforesaid dissolved uncomplexed saturated hydrocarbon from the membrane employed in aforesaid step (a), the resulting separated aqueous solution is subjected in step (c) to purification conditions such that each aforesaid unsaturated hydrocarbon complex remains substantially stable and dissolved in the aqueous phase but the dissolved, uncomplexed saturated hydrocarbon component comes out of solution and is removed from the aqueous solution. When the unsaturated hydrocarbon is ethylene or propylene, the purification conditions comprise a second temperature and a second pressure wherein the second temperature is in the range of from about −10° C. to about 300° C. and the second pressure is in the range of from about 0 to about 1000 pounds per square inch gauge, and wherein either the second temperature is from about 0° C., preferably from about 10° C., more preferably from about 15° C., to about 80° C., preferably to about 50° C., more preferably to about 35° C. above the first temperature employed in step (a), or the second pressure is from about 0, preferably from about 5, more preferably from about 10, to about 500, preferably to about 300, more preferably to about 50 pounds per square inch gauge below the first pressure employed in step (a), or both.

In one embodiment, step (c) comprises passing the aqueous solution separated in step (b) through a flash pot where the aqueous solution is subjected to the aforesaid purification conditions. In another embodiment, step (c) comprises contacting, through the micropores of another hydrophobic microporous hollow fiber membrane, the aqueous solution from step (b) flowing on the outer surface of the membrane with a gas phase on the interior of the membrane and containing a substantially lower concentration of the dissolved saturated hydrocarbon component than its concentration in the aqueous solution from step (b) under the aforesaid purification conditions.

The aqueous solution resulting from step (c) is then contacted under dissociation conditions, in step (d), with the outer surface of a hydrophobic microporous hollow fiber membrane, and through the micropores of the hydrophobic microporous hollow fiber membrane, with a gas phase in contact with the inner surface of the membrane and containing a substantially lower concentration of the unsaturated hydrocarbon than its equilibrium concentration in the aqueous solution from step (c), such that the aforesaid unsaturated hydrocarbon complex dissociates in the aqueous solution and the resulting dissociated unsaturated hydrocarbon is stripped into the gas phase. Preferably the gas phase is a stripping or purge gas flowing on the inside of the hollow fiber membrane. The dissociation conditions comprise a third temperature and a third pressure, wherein, when the unsaturated hydrocarbon is ethylene or propylene, the third temperature is in the range of from about −10° C. to about 300° C. and the third pressure is in the range of from about 0 to about 1000 pounds per square inch gauge and wherein either the third temperature is from about 0° C., preferably from about 10° C., more preferably from about 15° C., to about 80° C., preferably to about 50° C., more preferably to about 35° C., above the second temperature employed in step (c) or the third pressure is from about 0 preferably from about 5, more preferably from about 10 to about 500, preferably to about 300, more preferably to about 50 pounds per square inch gauge below the second pressure employed in step (c). Thereafter the resulting unsaturated hydrocarbon-rich gas phase is separated from the resulting unsaturated hydrocarbon-depleted aqueous phase in step (e).

In another embodiment of the process of the present invention, the feed gas contains two unsaturated hydrocarbons both of which form reversible soluble complexes with the complexing agent and dissolve in the aqueous solution in step (a) and both of such complexes remain stable and dissolved in the aqueous solution in step (c) wherein the aforesaid complexes have sufficiently different dissociation constants that one such complex dissociates and is stripped into the gas phase in step (d) while the other such complex remains stable and soluble in the aqueous solution resulting from step (d). In such embodiment, the process of the present invention comprises additionally; (f) separating the resulting aqueous solution from the membrane employed in step (d); (g) contacting, under more severe dissociation conditions than those employed in step (d) and through the micropores of a hydrophobic microporous hollow fiber membrane, the aqueous solution separated in step (f) and in contact with the outer surface of the membrane with a gas phase containing a substantially lower concentration of the aforesaid remaining complexed unsaturated hydrocarbon than its equilibrium concentration in the aqueous solution from step (f) and in contact with the inner surface of the membrane, such that such complex dissociates in the aqueous solution and the resulting dissociated unsaturated hydrocarbon is stripped into the gas phase; and (h) separating the resulting gas phase from the membrane employed in step (g). In such case, the dissociation conditions employed in step (g) comprise a fourth temperature and a fourth pressure, wherein, when the unsaturated hydrocarbon is ethylene or propylene, the fourth temperature is in the range of from about −10° C. to about 300° C. and the fourth pressure is in the range of from about 0 to about 1000 pounds per square inch gauge, and wherein either the fourth temperature is from about 0° C., preferably from about 10° C., more preferably from about 15° C., to about 80° C., preferably to about 50° C., more preferably to about 35° C. above the third temperature employed in step (d) or the fourth pressure is from about 5, preferably from about 10, more preferably from about 10, to about 500, preferably to about 300, more preferably to about 50 pounds per square inch gauge below the third pressure employed in step (d), or both.

Preferably, the gas phases employed in steps(c) (d) and (g) are each a stripping or purge gas that flows past one side of the membrane when the aqueous liquid solution flow passes the other side of the membrane. However, such gas phases can also each be stationary gas phase under vacuum or substantially reduced pressure. In any case, the gas phase in the form of a purge gas may promote purification in step (c) or dissociation in steps (d) or (g) even without a change in the temperature or pressure.

Figure 2:
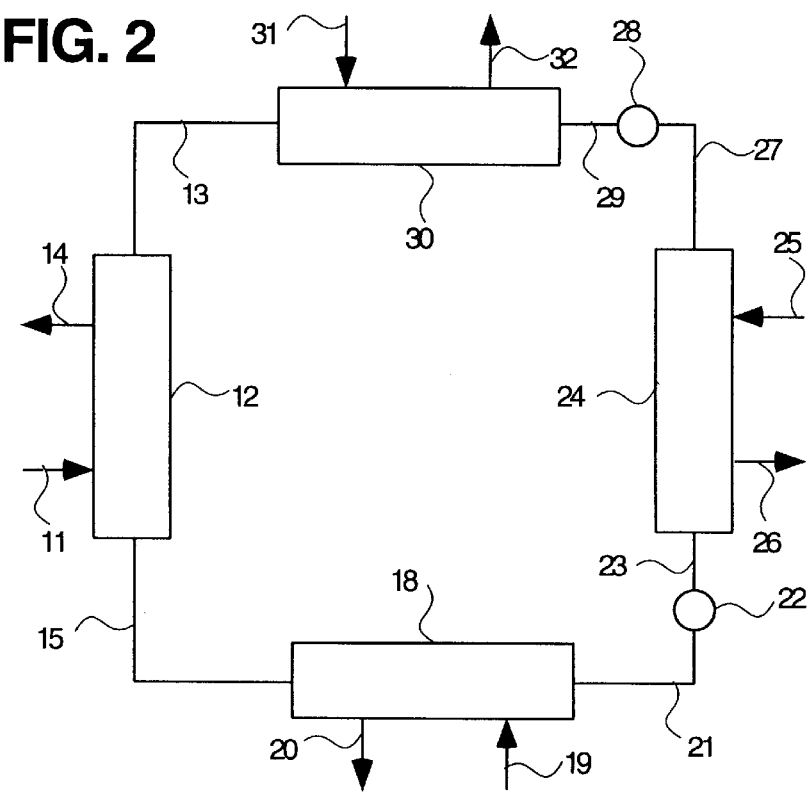
FIG. 2 is a schematic illustration of another preferred embodiment of the process of the present invention in which two unsaturated hydrocarbons are separated from a saturated hydrocarbon in a multi-component feed gas and are purified and separately recovered.

Two preferred embodiments of the process of this invention are illustrated schematically in FIGS. 1 and 2. It must be pointed out that FIGS. 1 and 2 are schematic representations and therefore that various features which are conventional parts of a process plant or which are not essential to an understanding of the present invention are not shown in FIGS. 1 and 2. Various alternatives and additional process steps are also not shown.

Turning now to FIGS. 1 and 2, one preferred embodiment of the process of this invention is shown in FIG. 1. In such embodiment, a fresh supply of a multi-component feed gas containing both unsaturated and saturated hydrocarbons is introduced through line 11 into module 12 containing a plurality of hydrophobic microporous hollow fiber membranes (not shown) and into the interior of each of the hollow fiber membranes therein. An aqueous solution of a suitable metal-containing complexation agent is introduced through line 13 into module 12 through which it flows in contact with the outer surface of each of the hollow fiber membranes therein through which the feed gas is flowing. The feed gas enters the pores of the hollow fiber membranes and comes into contact with the aqueous solution of the complexation agent at the interface between such solution and the outer surface of each hollow fiber membrane, under temperature and pressure conditions at which the unsaturated hydrocarbon forms a complex with the complexation agent and is thereby solubilized in the aqueous solution and a portion of the uncomplexed saturated hydrocarbon also dissolves in the aqueous solution. The resulting gas phase which is substantially depleted in the unsaturated hydrocarbon and partially depleted in the saturated hydrocarbon passes out of the hollow fiber membranes and is withdrawn from the module 12 through the line 14.

The resulting aqueous solution containing both the dissolved complex of the unsaturated hydrocarbon and the aforesaid dissolved uncomplexed saturated hydrocarbon is withdrawn from the module 12 through the line 15 and introduced thereby into the module 18 which also contains a plurality of hydrophobic microporous hollow fiber membranes. A stripping gas is introduced through line 19 and into the interior of each of the aforesaid hollow fiber membranes therein. The aqueous solution from line 15 passes through the module 18 in contact with the outer surfaces of the hollow fiber membranes therein. The stripping gas introduced through the line 19 into the module 18 is at a lower total pressure than that on the multi-component feed gas in the module 12 and contains none or a lower partial pressure of the saturated hydrocarbon than in the aqueous solution introduced into the module 18 from the line 15, as a result of which saturated hydrocarbon comes out of solution and passes from the aqueous solution in the module 18 through the hollow fiber membranes therein and into the stripping gas, which is then removed from the module 18 through the line 20.

The resulting aqueous solution from which saturated hydrocarbon has been substantially completely removed is then withdrawn from the module 18 through the line 21 to a heat exchanger 22 where the temperature of the aqueous solution is raised to a level at which the complex dissociates. The resulting warmer aqueous solution is then introduced through line 23 to the module 24 which also contains a plurality of hydrophobic microporous hollow fiber membranes. A stripping gas is introduced through the line 25 into the module 24 and into the interior of each of the aforesaid hollow fiber membranes therein. The aqueous solution from line 23 passes through the module 24 in contact with the outer surfaces of the aforesaid hollow fiber membranes. The stripping gas introduced through the line 25 is at the same total pressure as the stripping gas introduced into the module 18 through the line 19 and contains either no or a substantially lower concentration of the unsaturated hydrocarbon than its equilibrium concentration in the aqueous solution introduced through the line 23. At the higher temperature of the aqueous solution introduced through the line 23 into the module 24, the complex of the unsaturated hydrocarbon dissociates and the resulting dissociated unsaturated hydrocarbon passes from the aqueous solution through the membranes and into the stripping gas at the interface between the aqueous solution and the outer surface of each aforesaid hollow fiber membrane. The resulting stripping gas containing the unsaturated hydrocarbon is then withdrawn from the module 24 in the line 26. The resulting aqueous solution which is substantially free of both the aforesaid unsaturated hydrocarbon and the saturated hydrocarbon is then recycled through the line 13 to the module 12.

Another preferred embodiment of the process of this invention is shown in FIG. 2. Elements in the embodiment of FIG. 2 that correspond to elements in the embodiment of FIG. 1 are numbered the same as the corresponding elements in the embodiment of FIG. 1. Elements in the embodiment of FIG. 2 which function as do corresponding elements in the embodiment of FIG. 1 will not be described further. The essential difference between the embodiments of FIGS. 1 and 2 is that the multi-component feed gas introduced through line 11 in FIG. 2 contains two unsaturated hydrocarbons which are to be recovered separately. Thus, in the embodiment of FIG. 2, both such unsaturated hydrocarbons form soluble complexes with the complexation agent in the aqueous solution that is introduced in the line 13 into the module 12 and both such dissolved complexes are withdrawn from the module 12 in the aqueous solution in line 15. Both such unsaturated hydrocarbons remain in the form of their soluble complexes in the aqueous solution that passes out of the module 18 in the line 21. As a result of differences in the dissociation constants of such complexes, when the aqueous solution is heated in the heat exchanger 22, one of such complexes dissociates and the resulting dissociated unsaturated hydrocarbon is stripped from the aqueous solution in the module 24 and withdrawn therefrom in the stripping gas in line 26.

The other complex remains dissolved in the aqueous solution in the module 24 and is withdrawn therefrom in the line 27 and passed to the heat exchanger 28 where the temperature of the aqueous solution is raised to a higher level at which such complex dissociates. The aqueous solution is then introduced in the line 29 into the module 30 which also contains a plurality of microporous hydrophobic hollow fiber membrane. A stripping gas is introduced through the line 31 into the module 30 and into the interior of each of the aforesaid hollow fiber membranes therein. At the interface between the aqueous solution and the outer surface of the aforesaid hollow fiber membranes, the dissociated second unsaturated hydrocarbon passes from the aqueous solution into the stripping gas through the pores of the hollow fiber membranes and is withdrawn from the module 30 through the line 32. The aqueous solution of the complexation agent which at this point is substantially free of both the first unsaturated and second unsaturated hydrocarbons and the saturated hydrocarbon is withdrawn from the module 30 and recycled in the line 13 to the module 12.

The present invention will be more clearly understood from the following specific examples. While the invention is described in connection with the specific examples below, it is to be understood that these are for illustrative purposes only. Many alternatives, modifications and variations will be apparent to those skilled in the art in the light of the examples below, and such alternatives, modifications and variations fall within the scope and spirit of the appended claims.

EXAMPLE 1

In Example 1, the flow scheme illustrated in FIG. 1 was employed except that the module 18 was replaced by a flash pot and nitrogen as a purge gas was introduced through the line 19 into the aqueous solution in the flash pot, and the heat exchanger 22 was not employed. The hydrophobic microporous hollow fiber membranes employed in each of the modules 12 and 24 were identical polypropylene hollow fiber contactors obtained from Hoechst Celanese Corporation. Each such contactor contained about 10,000 fibers, each of which had an internal diameter of 240 microns and a pore size of 0.05 micron. Each such contactor had an effective surface area of 15 square feet and an overall porosity of 40 percent. The feed gas employed was a mixture of propylene and propane having a propylene selectivity—that is, the molar ratio of propylene to propane—of 0.11 and had been diluted with nitrogen such that the concentration of propylene in the feed gas was 1.61 mole percent.

The feed gas at 61° F. and 55 pounds per square inch absolute was introduced into the module 12 at a rate of 2.4 pounds per hour and into contact with the outer side of the hollow fibers therein. The complexation agent employed was a one molar aqueous liquid solution of silver nitrate at 52° F. and 64 pounds per square inch absolute and was introduced into the module 12 at a rate of 1.57 liters per minute and into the interior of the hollow fibers therein.

The gaseous effluent in line 14 from the module 12 had a propylene selectivity of 0.037. The pressure on the aqueous solution of complexed propylene withdrawn from the module 12 in line 15 was reduced to 19 pounds per square inch absolute and introduced into the flash pot wherein nitrogen purge gas at 0.83 pound per minute was in contact with the aqueous solution to remove therefrom any dissolved uncomplexed propane. The gaseous effluent from the flash pot had a propylene selectivity of 0.087. The aqueous solution was then withdrawn from the flash pot through the line 21 and introduced into the module 24 and into the interior of the hollow fibers therein. Nitrogen was introduced into the module 24 at a rate of 3 pounds per hour and into contact with the outer side of the hollow fibers therein. The gaseous effluent from the module 24 in line 26 had a propylene selectivity of 10.9.

The overall propylene flux was 6.75 standard liters per hour per square meter of surface area of the hollow fibers in the module 24, and the overall propylene recovery was 68 mole percent.

EXAMPLE 2

In Example 2, the procedure, materials, parameters and apparatus of Example 1 were employed, except as indicated herein. A mixture of propylene and propane containing 50 mole percent of propylene and no nitrogen and having a propylene selectivity of 1 was employed as the feed gas. The feed gas at 60.2° F. and 52.3 pounds per square inch absolute was introduced into the module 12 at a rate of 2.7 pounds per hour and into the interior of the hollow fibers therein. The aqueous solution of the complexation agent at 57.7° F. and 57.7 pounds per square inch absolute was introduced into the module 12 at a rate of 0.9 liter per minute and into contact with the outer side of the hollow fibers therein. The gaseous effluent in line 14 from the module 12 had a propylene selectivity of 0.19.

The flash pot was purged with nitrogen at a rate of 0.084 pounds per hour, and the gaseous effluent from the flash pot had a propylene selectivity of 1.82. Nitrogen purge gas was introduced into the module 24 at a rate of 1.3 pounds per hour, and the propylene selectivity in the gaseous effluent withdrawn from the module 24 in line 26 was 85.8. The overall propylene flux was 17.8 standard liters per hour per square meter of surface area of the hollow fibers in module 24, and the overall propylene recovery was 81 mole percent.

From the above description, it is apparent that the objects of the present invention have been achieved. While only certain embodiments and various modifications have been described, numerous alternative embodiments and various modifications will be apparent from the above description to those skilled in the art. These alternatives and embodiments are considered equivalents and within the spirit and scope of the present invention.

Having described the invention, what is claimed is:

1. A process for the separation, purification and recovery of an unsaturated hydrocarbon from a mixture thereof with at least one other component in a multi-component feed gas, comprising:

(a) contacting, through the micropores of a first hydrophobic microporous hollow fiber membrane, the feed gas flowing on one side of the membrane and an aqueous liquid solution of a complexation agent flowing on the other side of the membrane, under conditions (i) such that the aforesaid complexation agent has a substantially greater affinity to form, and does selectively form a reversible water soluble complex with the aforesaid unsaturated hydrocarbon such that a substantial portion of the unsaturated hydrocarbon dissolves in the aqueous solution, and (ii) such that a portion of at least one other uncomplexed component of the feed gas dissolves in the aqueous solution;

(b) separating the resulting aqueous solution from the membrane employed in step (a);

(c) contacting, through the micropores of a third hydrophobic microporous hollow fiber membrane, the aqueous solution separated in step (b) flowing on one side of the third membrane with a gas phase on the other side of the third membrane and containing a substantially lower concentration of the aforesaid uncomplexed component than in the aqueous solution from step (b), under conditions such that the solubility of the aforesaid uncomplexed component in the aqueous solution is substantially reduced and the uncomplexed component is substantially stripped into the aforesaid gas phase, and the aforesaid complex of the unsaturated hydrocarbon remains substantially stable and dissolved in the aqueous solution;

(d) contacting, through the micropores of a second hydrophobic microporous hollow fiber membrane, the aqueous solution resulting from step (c) and flowing on one side of the second membrane with a gas phase on the other side of the second membrane and containing a substantially lower concentration of the aforesaid unsaturated hydrocarbon than its equilibrium concentration in the aqueous solution from step (c), under conditions such that the aforesaid complex substantially dissociates in the aqueous solution and the resulting dissociated unsaturated hydrocarbon is substantially stripped into the gas phase on the other side of the second membrane; and (e) separating the resulting gas phase from the membrane employed in step (d).

2. The process of claim 1 wherein step (c) comprises passing the aqueous solution separated in step (b) through a flash pot where the aqueous solution is subjected to the aforesaid purification conditions.

3. The process of claim 1 wherein the gas phase employed in step (d) is a stripping gas flowing on the aforesaid other side of the aforesaid second membrane.

4. The process of claim 1 wherein the gas phase employed in step (c) is a stripping gas flowing on the aforesaid other side of the aforesaid third membrane.

5. The process of claim 1 wherein the conditions employed in step (a) comprise a first temperature and a first pressure and wherein the first temperature is in the range of from about −10° C. to about 300° C. and the first pressure is in the range of from about 0 to about 1000 pounds per square inch gauge.

6. The process of claim 5 wherein the first temperature is in the range of from about 0° C. to about 250° C.

7. The process of claim 5 wherein the first pressure is in the range of from about 25 to about 600 pounds per square inch gauge.

8. The process of claim 5 wherein the purification conditions employed in step (c) comprise a second temperature and a second pressure, wherein the second temperature is in the range of from −10° C. to about 300° C. and the second pressure is in the range of from about 0 to about 1000 pounds per square inch gauge and wherein either the second temperature is from about 0° C. to about 80° C. higher than the first temperature employed in step (a) or the second pressure is from about 5 to about 500 pounds per square inch gauge below the first pressure employed in step (a), or both.

9. The process of claim 8 wherein the second temperature is from about 10° C. to about 50° C. higher than the first temperature employed in step (a).

10. The process of claim 8 wherein the second pressure is from about 10 to about 300 pounds per square inch gauge lower than the first pressure employed in step (a).

11. The process of claim 8 wherein the conditions employed in step (d) comprise a third temperature and a third pressure, wherein the third temperature is in the range of from about −10° C. to about 300° C. and the third pressure in the range of from about 0 to about 1000 pounds per square inch gauge and either the third temperature is from about 0° C. to about 80° C. higher than the second temperature employed in step (c) or the third pressure is from about 5 to about 500 pounds per square inch gauge below the second pressure employed in step (c), or both.

12. The process of claim 11 wherein the third temperature is from about 10° C. to about 50° C. higher than the second temperature employed in step (c).

13. The process of claim 11 wherein the third pressure is from about 10 to about 300 pounds per square inch gauge lower than the second pressure employed in step (c).

14. The process of claim 1 wherein the feed gas contains two unsaturated hydrocarbons both of which form reversible soluble complexes with the complexing agent and dissolve in the aqueous solution in step (a) and both of such complexes remain stable and dissolved in the aqueous solution in step (c), wherein the aforesaid complexes have sufficiently different dissociation constants and the conditions are maintained in step (d) such that one such complex dissociates and is stripped into the gas phase in step (d) while the other such complex remains stable and soluble in the aqueous solution resulting from step (d), and wherein the process comprises additionally:

(f) separating the resulting aqueous solution from the membrane employed in step (d);

(g) contacting, under more severe dissociation conditions than those employed in step (d) and through the micropores of a fourth hydrophobic microporous hollow fiber membrane, the aqueous solution separated in step (f) flowing on one side of the fourth membrane with a gas phase on the other side of the fourth membrane and containing a substantially lower concentration of the unsaturated hydrocarbon in the aforesaid complexed unsaturated hydrocarbon than its equilibrium concentration in the aqueous solution from step (f), such that such complex dissociates in the aqueous solution and the resulting dissociated unsaturated hydrocarbon is stripped into the aforesaid gas phase; and (h) separating the resulting gas phase from the membrane employed in step (g).

15. The process of claim 14 wherein the gas phase employed in step (d) is a stripping gas flowing on the aforesaid other side of the aforesaid second membrane and the gas phase employed in step (g) is a stripping gas flowing on the aforesaid other side of the fourth membrane.

16. The process of claim 1 wherein the unsaturated hydrocarbon separated comprises at least one of ethylene and propylene and the aforesaid other material in the feed gas comprises at least one of ethane, propane, hydrogen and methane.

17. The process of claim 1 wherein the membranes employed in steps (a) and (d) are each a polysulfone, polypropylene or polyethylene or a copolymer of ethylene or propylene.

* * * * *